United States Patent [19]
Sydor et al.

[11] Patent Number: 5,388,273
[45] Date of Patent: Feb. 14, 1995

[54] SUPPORT STAY

[75] Inventors: Robin M. Sydor; Thomas M. Grimm, both of Robbinsdale, Minn.

[73] Assignee: Ergodyne Corporation, St. Paul, Minn.

[21] Appl. No.: 14,106

[22] Filed: Feb. 5, 1993

[51] Int. Cl.$^6$ .................... A41C 1/12; A41D 27/00; A61F 5/00
[52] U.S. Cl. .............................................. 2/255; 2/44; 2/256; 2/258; 128/112.1; 128/115.1; 450/143; 450/144; 450/155; 602/19
[58] Field of Search .................. 2/69, 69.5, 44, 22, 2/45, 23, 46, 24, 92, 94, 113, 115, 267, 268, 255, 256, 257, 258, 259, 260, 260.1, 261, 262, 263; 450/155, 143, 144, 137, 138, 139; 602/19; 128/115.1, 112.1

[56] References Cited

U.S. PATENT DOCUMENTS

| | | | |
|---|---|---|---|
| 603,932 | 5/1898 | Tucker | 128/115.1 |
| 627,807 | 6/1899 | Harrington | 128/115.1 X |
| 1,606,214 | 11/1926 | Ferron | 128/115.1 |
| 1,918,590 | 7/1933 | Burton | 128/112.1 X |
| 1,925,615 | 9/1933 | Stuart | 128/112.1 X |
| 3,931,816 | 1/1976 | Waldmann | 450/155 X |
| 3,970,079 | 7/1976 | Gaylord, Jr. | 128/78 |
| 4,441,211 | 4/1984 | Donzis | 2/69 X |
| 4,884,562 | 12/1986 | Stone | 128/78 |
| 5,040,524 | 8/1991 | Votel et al. | 128/78 |
| 5,072,725 | 12/1991 | Miller | 128/78 |
| 5,111,906 | 5/1992 | Travis | 602/19 |
| 5,148,549 | 9/1992 | Sydor | 2/44 |
| 5,250,345 | 10/1993 | Chu | 2/268 |
| 5,274,846 | 1/1994 | Kolsky | 2/267 X |

OTHER PUBLICATIONS

Copy of European Search Report for EP Appln. No. 93 20 2725.

Primary Examiner—Jeanette E. Chapman
Attorney, Agent, or Firm—Merchant, Gould, Smith, Edell, Welter & Schmidt

[57] ABSTRACT

A support stay for use with an article to be worn by a person has two durometers of hardness. The support stay includes a base member having a first hardness, the first hardness sufficient to provide a required rigidity for support. A gripping member is operatively connected to the base member. The gripping member has a second hardness which is softer than the first hardness. The gripping member, when attached to the inner surface of the article, provides a non-slip surface against the person wearing the article to keep the article in position.

21 Claims, 3 Drawing Sheets

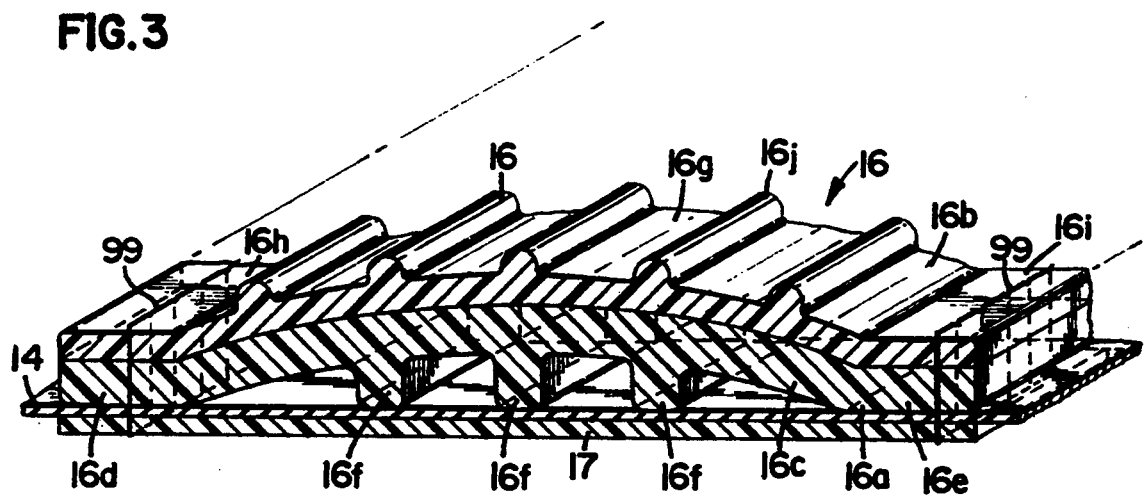

SUPPORT STAY

BACKGROUND OF THE INVENTION

1. Field of the Invention

This invention related generally to support stays and more particularly to a dual durometer support stay for use with an article to be worn by a person.

2. Description of the Prior Art

Support stays have been utilized in a variety of articles, such as wrist supports, ankle braces, and back supports, as well as many other similar and related products. The function of the support has been to provide added rigidity for the article with which it is used. These stays have been made from a variety of materials.

In addition to providing rigidity, for certain articles, it is important to maintain the article being worn in a certain position on the wearer's body. One example of such a product is a back support, such as those disclosed in U.S. Pat. Nos. 5,040,524 and 5,148,549. In those back supports, the stays are enclosed in a pocket. In addition, in certain embodiments, these back supports have a material which has a rubber texture over the stay pockets so that the support will stay in position on the wearer. It can be seen that the stays have two functional and performance characteristics. The first is that the stainless steel stays give vertical spinal support and prevents the back support from gathering and "rolling over" as the support moves around the body. The second is the grabbing or anti-skid properties of the rubber material over the stay pockets. This grabbing or gripping inhibits the back supports from "riding up" on the body and improperly supporting the vulnerable regions of the abdomen and lower back. While this has proven to be an effective back support, there are certain problems which are associated with a stay being incorporated in the back support in such a manner. Since a pocket for the stay is used, the stay can slide freely within the pocket. This movement can lead to problems. These problems include that the metal stays may poke through the pocket in which they are positioned and also the movement may cut the rubber threads in the rubber material. Another problem is that the rubber threads may become frayed. Still further, there are multiple components which add additional cost and time in the manufacturing of the back support. In addition, when metal supports are utilized, they also make the back support conductive of electricity.

The present invention addresses the drawbacks of the prior art and provides for an improved support stay which may be incorporated in articles to be worn by a person.

SUMMARY OF THE INVENTION

The invention is a support stay for use with an article to be worn by a person. The article has an outer surface and inner surface. The inner surface is proximate the person when the article is worn. The stay includes a base member having a first hardness. The first hardness is sufficient to provide a required rigidity for providing support. A gripping member is operatively connected to the base member. The gripping member has a second hardness which is softer than the first hardness. The gripping member, when attached to the inner surface of the article, provides a non-slip surface against the person wearing the article to keep the article in position. In the preferred embodiment, the base member and gripping member are co-extruded plastic members and the base is constructed of a polypropylene material and the gripping member is a mixture of polypropylene and rubber. Further, in a preferred embodiment, the base member has a curved cross-section and a plurality of ribs for additional rigidity and a gripping enhancement means is operatively connected to the gripping member.

In another embodiment, the invention is a back support for providing abdominal and lumbosacral support as needed by the wearer. The back support includes a waistband of a construction having a limited amount of stretch, the waistband having first and second ends and inner and outer surfaces. Also provided is a means for releasably connecting the first end to the second end so that the waistband surrounds a wearer's lower back. An elastic band is operatively connected to the outer surface of the waistband. The elastic band has first and second ends releasably connected to the outer surface so as to be easily moved between an unstretched and a stretched position. A plurality of support stays are operatively connected to the waistband and positioned on the inner surface. The stay includes a base member having a first hardness. The first hardness is sufficient to provide a required rigidity for providing support. A gripping member is operatively connected to the base member and the gripping member has a second hardness which is softer than the first hardness. The gripping member provides a non-slip surface against the person wearing the back support to keep the back support in position on the wearer.

BRIEF DESCRIPTION OF THE DRAWINGS

FIG. 3 is an enlarged perspective view of a cross-section of the back support shown in FIG. 1.

DETAILED DESCRIPTION OF THE PREFERRED EMBODIMENT

Figure 1:
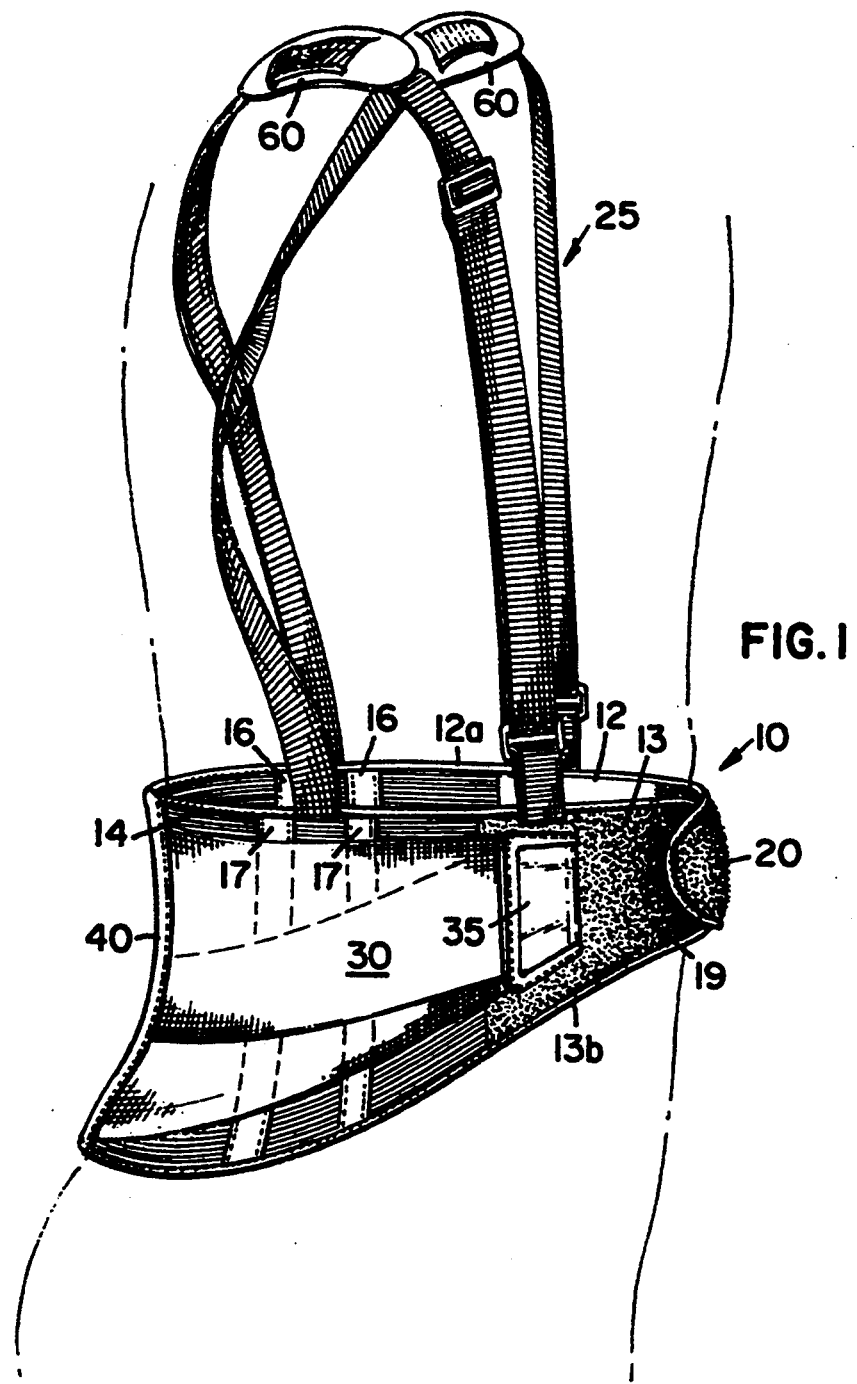
FIG. 1 is a perspective view of the back support of the present invention.

As shown in the drawings, wherein like numerals represent like parts throughout the several views, there is generally disclosed at 10 a back support. The back support 10 includes a waistband 11 having a left half 12 and a right half 13. While this is referred to as a waistband, it is understood that the waistband 11 is designed to rest below the navel and accordingly is not defined as being literally a band around the waist, but also may be below the waist. A piece of fabric 14, is cut to the size of the entire waistband 11. Depending upon the embodiment of the invention to be constructed, the fabric 14 may be made of either a stretchable or unstretchable fabric. As will be discussed more fully hereafter, in one embodiment it is desired to have some stretchability to the waistband 11, while in other embodiments, such as when a tool belt is hung from the back support, it is desirable to not have any stretch to the waistband 11. If a stretchable material is desired, a suitable material, such as spandex, may be utilized. If it is desired to have a non-stretchable fabric, any suitable material, such as apex, may be utilized. A ribbing or binding 18 is stitched around the periphery of the entire waistband 11. A loop fabric 19 is stitched to the outside of the right half 13 and a loop fabric 20 is stitched to the outside of the left half 12. On the inside of the left half 12 of the waistband 11, a hook material 21 is secured by stitching. The hook material 21 and loop fabric 19 and 20 may be of any type well-known in the industry which would form a hook and loop type fastener such as Velcro brand. The fabric 14 may be somewhat stretchable, however, the fabrics 19 and 20 are substantially non-stretchable. The fabric 14 may be suitable material such as the made stretchable Spandex® material. The binding 18 may be made of a suitable material such as tricot. As previously stated, if a stretchable material such as spandex is utilized, the overall waistband will have some stretchability. For instance, with a waistband 11 having an overall length of approximately 42 inches, the waistband 11 may expand from ½ to 3 inches and preferably from 1 ½ to 2 inches. This allows the waistband 11 to have the capabilities of stretching and conforming to the body of the wearer. The waistband 11 has a top edge 12a and 13a and a bottom edge 12b and 13b. As can be seen in the drawings, the right half 12 and the left half 13 form a generally V-shaped waistband 11. As shown in the drawings, each half 12 and 13 form an angle of approximately 13° with a horizontal line although in other embodiments there may be no angle. Adjustable suspenders, generally designated as 25, are secured to the top edge 12a and 13a of the waistband 11. The suspenders 25 may be of any type well known in the art and have shoulder pads 60. Also, the suspenders may be detachable. In another embodiment the waistband 11 may have a fibrous material laminated thereto to allow heat and moisture to be transferred away from the body of the wearer. Such a suitable fabric may be a Coolmax ™ fabric by DuPont. The fabric is simply laminated to the waistband 11 such that the fabric is adjacent the wearer of the body. Alternately, instead of being laminated to the waistband 11, the fabric (Coolmax) may be used in place of the Spandex® material forming the waistband 11.

A four inch wide elastic band, designated generally as 30, has a top four inch band 31 and a bottom four inch band 32. The top band 31 is generally rectangular but has a slight V-shape and the bottom band 32 has more of a V-shape. The bands 31 and 32 are connected to each other at their ends and at the left end of bands 31 and 32 are connected by a vinyl piece 33 on the outside surface and a hoop material 34 on the bottom surface. Similarly, the right ends are connected and has a vinyl piece 35 and a hoop material underneath (not shown). The vinyl pieces 33 and 35 may also by any suitable material which is easily cleaned and is durable such as rubber or polyurethane. A loop 40 has a first end operatively connected, such as by stitching 42, proximate the top surfaces 12a and 13a and a second end operatively connected, such as by stitching 43, proximate the bottom edges 12b and 13b. This loop 40 is shown in more detail in FIG. 4. The top stitching 42 and bottom stitching 43 only fastens the ends of the loop 40 to the waistband 11. Accordingly, there is an opening between the waistband and the underneath side of the loop through which the elastic band 30 may be positioned. Each of the bands 31 and 32 may be of any suitable length, such as approximately 24 inches when not stretched. When stretched, this length may be increased to a suitable length so as to provide the necessary support. While the specific design of the support will dictate the length of the stretch desired, it has been found that from 5 to 15 inches and preferably from about 9 to 13 inches and still more preferably 10 to 12 inches of stretch is desirable.

In operation, the wearer places the suspenders 25 over her shoulders so that the right side 13 is on her right side and the left side 12 is on her left side. Then, the tension of the elastic band 30 is released by removing the ends of the elastic band away from the fabric 20 and 19. The elastic band 30, at this point, is held in position only by the loop 40 with the ends of the elastic band 30 hanging free. Then, the wearer grasps each end of the waistband 11 and stretches the right end 13 across the left end and places the hook material 18 on top of the fabric 19 to secure the waistband in position. It is important that the waistband 18 firmly supports the lower back/upper buttocks. The upper edge of the waistband 12a and 13a should be below the navel.

The wearer then continues to wear the back support with the elastic band 30 having its end either loose or attached to the fabrics 19 and 20 in an unstretched state. Then, just before lifting, the ends are grabbed at locations 33 and 35 and stretched as far forward as possible, and then placed against the fabric 19 and 20 so that the hook material 34 on the left side and the hook material on the comparable right side fastens the elastic band in a stretched position.

The back support structure and operation, described so far, is well known in the art. Further, the invention with respect to the support stays to be described hereafter, is applicable not only to the type of back support described above, but is also understood that the support stays may be used with other style back supports and other articles requiring support.

Figure 2:
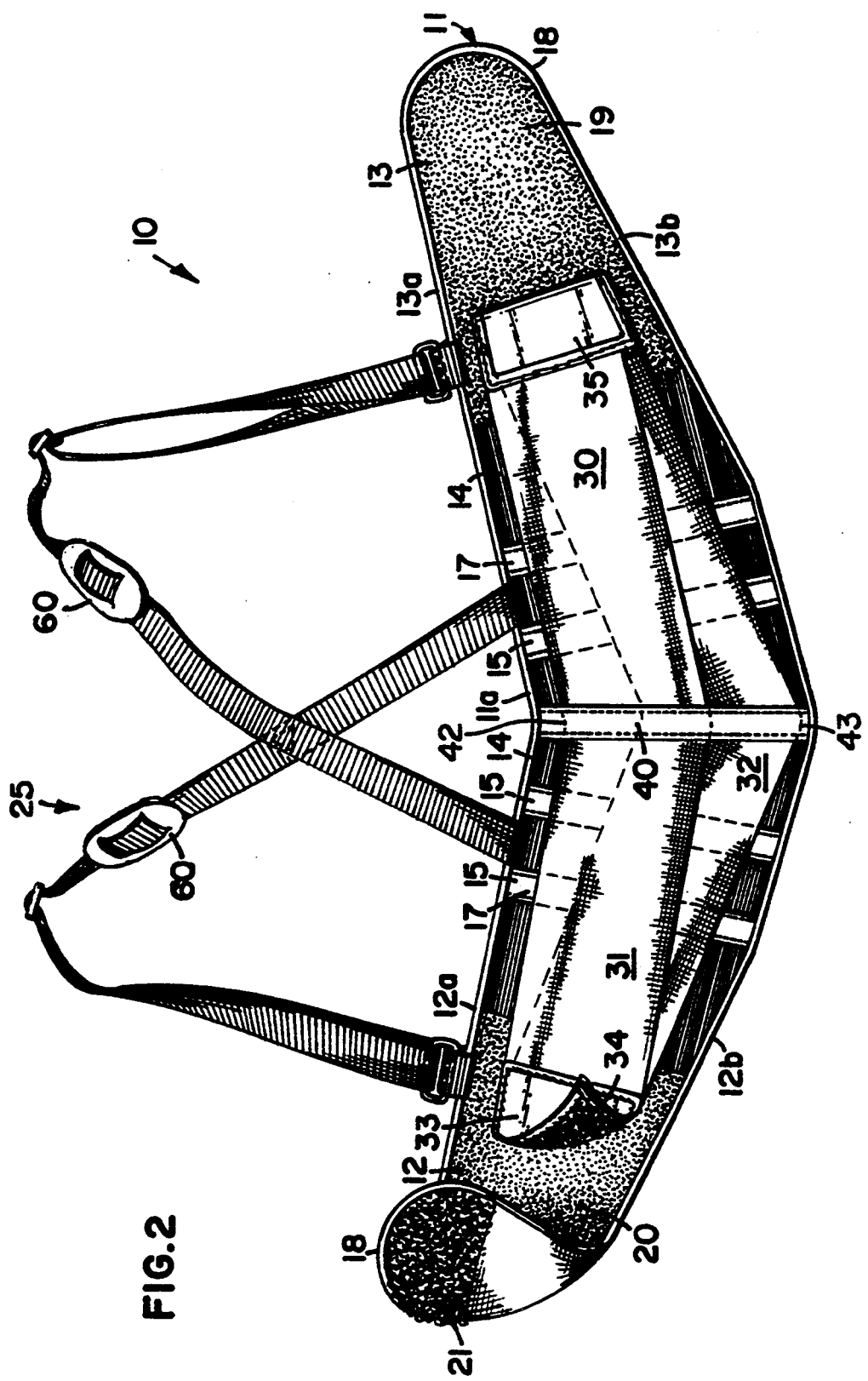
FIG. 2 is a front elevational view of the back support shown in FIG. 1, with the back support being in an unfolded layout.

The stay is generally designated at 16 and is shown on the back support in FIGS. 1 and 2 and in more detail in FIG. 3. The stay, generally designated as 16, includes a base member 16a and a gripping member 16b operatively connected to the base member 16a. The base member 16a has a generally curved cross-section 16c for added rigidity. The base member has two flanges 16d and 16e operatively connected to the curved section 16c at each end. The curved section provides for increased rigidity without using as much material as would be required if the base member was flat. Still further, a plurality of ribs 16f are operatively connected to the base member 16a again for increased rigidity. The gripping member 16b has a profile which matches the base member 16a. That is, there is a center section 16g and operatively connected at its two ends are two flanges 16h and 16i. A plurality of elongate ribs 16j are operatively connected to the outer surface of the curved section 16g. The rib 16j, as will be described more fully hereafter, provide for gripping enhancement. As shown in FIG. 3, the stays are attached to the fabric 14 of the back support by any suitable means such as stitching. This method of attachment is shown in FIG. 3 wherein the stay 16 is attached by means of stitches 99 to fabric 14. A strip of fabric material 17 is on the opposite side of the fabric 14 than the stay and the stitching 99 goes through the stay 16, fabric 14 and strip 17. The strip 17 may be any suitable fabric such as a leather-like material or webbing. Still further, the stay may be connected without the use of the strip material 17. It is also understood that other suitable means besides sewing could be utilized, such as heat transfer, adhesives, rivets, staples, tape or other fastening techniques.

Preferably, the stay 16 is a single component and is manufactured by dual extrusion process. It is necessary that this stay provides a necessary rigidity to provide proper support while still having a high coefficient of drag to prevent "riding up". To obtain a high coefficient of drag, the material needs to be flexible which is the opposite of the requirement for a rigid support. The present invention combines both of these properties into one integral unit that can be easily sewn in place. The base member 16a (which includes the flanges 16d and 16e and the ribs 16f) is constructed of a material which has more rigidity, such as a rigid thermoplastic like polypropylene. The base member has a hardness of from 65 to 85 Rockwell hardness and preferably 70 R–80 R and more preferably 75 R. Further, the base 16a has been designed with a curved section 16c and a plurality of ribs 16f which design provides more rigidity while requiring less material. The gripping member 16b (which includes the flanges 16h and 16i and the ribs 16j) is constructed from a softer material such as a blend of polypropylene and rubber, such as that sold under the brand name Santoprene. Preferably, a grade 7823 polypropylene is utilized and a 101-64 Santoprene is utilized. This is a Santoprene with a 64 durometer on the Shore A scale. However, it has been found that a hardness of from 55 to 73, Shore A scale is acceptable for providing a gripping member preferably from 60–70 Shore A. Still further, a plurality of projection 16j are on the top portion of the gripping member 16b, thereby providing a gripping enhancement to the gripping member 16b. By using a dual extrusion process, the properties of the two different materials are able to be combined and to integrate them into one component, avoiding problems associated with individual components and allowing for easier assembly during the manufacturing. The dual extrusion process combined two materials from the olefin family, polypropylene and Santoprene, which as previously stated, is a polypropylene base material with a rubber additive. The polypropylene gives the rigid characteristics and the Santoprene with its rubber additive provides the stay with its grabbing properties. To process the stay, the two materials are extruded separately and they pass through the dual extrusion die which configures the material into the desired cross-section. Being composed of the same base material, the two materials bond together and are permanently bonded. The process is void of any adhesives or solvents and the two materials cannot be separated without destroying the integrity of the materials. While this is the preferred embodiment, it is also understood that the stay may be made by alternate methods. These methods would include dual injected molding or extruding the two members separately and bonding them together with a suitable adhesive, tape or sewing them together in the back support. Still further, other rigid plastic materials such as ABS, polyethylene, nylon, polystyrene and the like may be used as well as other rubber-like materials may be utilized for the gripping member 16b. These rubber-like materials could include TPR, vyram, silicone, rubber, crayton, thermoplastic elastomers, rubber like plastics and the like. It is of course also understood that other cross-sections could be utilized as well as different gripping enhancement means. Instead of the ribs 16j, there could be textured surface by way of squiggles, dots, or secondary operations such as calendaring could be used to increase the coefficient of drag.

As shown in the Figures, the stay 16 has an overall width of approximately 1 inch and a length of approximately 8 inches, while it is understood that other suitable dimensions may be utilized.

Other modifications of the invention will be apparent to those skilled in the art in light of the foregoing description. This description is intended to provide specific examples of individual embodiments which clearly disclose the present invention. Accordingly, the invention is not limited to these embodiments or the use of elements having specific configurations and shapes as presented herein. All alternative modifications and variations of the present invention which follow in the spirit and broad scope of the appended claims are included.

We claim:

1. A support stay for use with an article to be worn by a person, the article having an outer surface and an inner surface, the inner surface proximate the person when worn, the stay comprising:
    (a) a base member having a first hardness, said first hardness sufficient to provide a required rigidity for providing support;
    (b) a gripping member operatively connected to said base member;
    (c) said gripping member having a second hardness which is softer than said first hardness;
    (d) said gripping member, when attached to the inner surface of the article, provides a non-slip surface against the person wearing the article to keep the article in position;
    (e) said gripping member has a durometer of from 55 to 73, Shore A scale;
    (f) wherein said base member has a durometer of from 65 to 85, Shore A scale; and
    (g) a gripping enhancement means operatively connected to said gripping member.

2. The support stay of claim 1, further comprising said base member and said gripping member are co-extruded plastic members as an integral one-piece unit.

3. The support stay of claim 2, further comprising said base member is polypropylene and said gripping member is a mixture of polypropylene and rubber.

4. The support stay of claim 1, further comprising said base member having a generally curved cross-section for added rigidity.

5. The support stay of claim 1, further comprising a plurality of ribs operatively connected to said base member for added rigidity.

6. The support stay of claim 1, further comprising said gripping enhancement means comprises a plurality of raised elongate members.

7. A back support for providing abdominal and lumbosacral support as needed by the wearer, comprising:
    (a) a waistband of a construction having a limited amount of stretch, said waistband having first and second ends and inner and outer surfaces;
    (b) means for releasably connecting said first end to said second end so that said waistband surrounds a wearer's lower back;
    (c) an elastic band operatively connected to said outer surface of said waistband, said elastic band having first and second ends releasably connected to said outer surface, so as to be easily moved between an unstretched and a stretched position; and
    (d) a support stay operatively connected to said waistband without the need of a pocket and positioned on said inner surface, comprising:
        (i) a base member having a first hardness, said first hardness sufficient to provide a required rigidity for providing support;
        (ii) a gripping member operatively connected to said base member;
        (iii) said gripping member having a second hardness which is softer than said first hardness; and
        (iv) said gripping member, when attached to the inner surface of the article, provides a non-slip surface in direct contact with the person wearing the article to keep the article in position.

8. The back support of claim 7, further comprising said gripping member having a durometer of from 55 to 73, Shore A scale.

9. The back support of claim 7, further comprising said base member having a durometer of from 65 to 85 Rockwell hardness.

10. The back support of claim 7, further comprising said base member and said gripping member are co-extruded plastic members.

11. The back support of claim 10, further comprising said base member is polypropylene and said gripping member is a mixture of polypropylene and rubber.

12. The back support of claim 7, further comprising said base member having a generally curved cross-section for added rigidity.

13. The back support of claim 12, further comprising a plurality of ribs operatively connected to said base member for added rigidity.

14. The back support of claim 7, further comprising a gripping enhancement means operatively connected to said gripping member.

15. The back support of claim 7, wherein said gripping enhancement means comprises a plurality of raised elongate members.

16. A back support for providing abdominal and lumbosacral support as needed by the wearer, comprising:
(a) a waistband of a construction having a limited amount of stretch, said waistband having first and second ends and inner and outer surfaces;
(b) means for releasably connecting said first end to said second end so that said waistband surrounds a wearer's lower back;
(c) an elastic band operatively connected to said outer surface of said waistband, said elastic band having first and second ends releasably connected to said outer surface, so as to be easily moved between an unstretched and a stretched position;
(d) a support stay operatively connected to said waistband without the need of a pocket and positioned on said inner surface, comprising:
(i) a base member having a hardness of from 65 to 85 Rockwell hardness, to provide rigidity for providing support;
(ii) a gripping member having a hardness of from 55 to 73, Shore A scale;
(iii) said base member and said gripping member are co-extruded plastic members;
(iv) said gripping member provides a non-slip surface in direct contact with the person wearing the back support to keep the back support in position.

17. The back support of claim 16, further comprising:
(a) said base member having a generally curved cross-section and a plurality of ribs operatively connected to said base member for added rigidity; and
(b) a plurality of raised elongate members operatively connected to said gripping means for enhancing gripping by said gripping means.

18. The back support of claim 17, further comprising said base member is made of polypropylene and said gripping member is a mixture of polypropylene and rubber.

19. An article to be worn by a wearer, the article comprising:
(a) a member for encircling a portion of the wearer, the member having inner and outer surfaces;
(b) means for releasably connecting the member around a portion of the wearer;
(c) a support stay operatively connected to said member without the need of a pocket and positioned on said inner surface, comprising:
(i) a base member having a first hardness, said first hardness sufficient to provide a required rigidity for providing support;
(ii) a gripping member operatively connected to said base member;
(iii) said gripping member having a second hardness which is softer than said first hardness; and
(iv) said gripping member provides a non-slip surface in direct contact with the person wearing the article to keep the article in position.

20. The article of claim 19, wherein said article is a back support.

21. The article of claim 19, wherein the back support includes a waistband, having inner and outer surfaces, that encircle the wearer's lower back, said stay is operatively connected to the inner surface to keep the back support in position.

* * * * *